US00PP27399P3

(12) United States Plant Patent
Stemkens

(10) Patent No.: US PP27,399 P3
(45) Date of Patent: Nov. 15, 2016

(54) ***LAVANDULA* PLANT NAMED 'LABZ0006'**

(50) Latin Name: *Lavandula stoechas*
Varietal Denomination: LABZ0006

(71) Applicant: SYNGENTA PARTICIPATIONS AG, Basel (CH)

(72) Inventor: Henricus Godefridus Wilhelmus Stemkens, Enkhuizen (NL)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 14/756,612

(22) Filed: Sep. 24, 2015

(65) Prior Publication Data

US 2016/0183443 P1 Jun. 23, 2016

Related U.S. Application Data

(60) Provisional application No. 62/090,543, filed on Dec. 11, 2014.

(51) Int. Cl.
*A01H 5/02* (2006.01)

(52) U.S. Cl.
USPC ..... Plt./445

(58) Field of Classification Search
USPC ..... Plt./445
See application file for complete search history.

(56) References Cited

PUBLICATIONS

PLUTO Plant Variety Database Sep. 2, 2016.p. 1.*

* cited by examiner

*Primary Examiner* — Annette Para
(74) *Attorney, Agent, or Firm* — Joshua L. Price

(57) ABSTRACT

A new *Lavandula* plant named 'LABZ0006', particularly distinguished by numerous rose-pink sterile large bracts, rose-pink flowers, medium green foliage without greyish hue, a fairly small sized plant with a rounded, mounding habit, early to flower and long flowering.

1 Drawing Sheet

Latin name of the genus and species of the plant claimed: *Lavandula stoechas.*

Varietal denomination: 'LABZ0006'.

BACKGROUND OF THE NEW PLANT

The present invention comprises a new *Lavandula*, botanically known as *Lavandula stoechas*, and hereinafter referred to by the variety name 'LABZ0006'.

'LABZ0006' is a product of a planned breeding program. The new cultivar has numerous rose-pink sterile large bracts, rose-pink flowers, medium green foliage without greyish hue, a fairly small sized plant with a rounded, mounding habit, is early to flower and long flowering.

'LABZ0006' originated from a pollination made in 2008 in a greenhouse in Enkhuizen, Netherlands. The female parent was the unpatented, proprietary plant designated 'LA-07-45-5', with a rose flower, compact habit, weak growth, and starting to flower 2 weeks later when compared to 'LABZ0006'.

The male parent of 'LABZ0006' is unknown.

The resultant seed was sown in January 2010 and grown outdoors in Enkhuizen, Netherlands. 'LABZ0006' was selected as a single flowering plant within the progeny of the stated cross on Jul. 23, 2010 in Enkhuizen, Netherlands.

The first act of asexual reproduction of 'LABZ0006' was accomplished when vegetative cuttings were propagated from the initial selection in April 2011 in a greenhouse in Enkhuizen, Netherlands.

BRIEF SUMMARY OF INVENTION

Horticultural examination of plants grown from cuttings of the plant initiated April 2011, and continuing thereafter, has demonstrated that the combination of characteristics as herein disclosed for 'LABZ0006' are firmly fixed and are retained through successive generations of asexual reproduction.

'LABZ0006' has not been observed under all possible environmental conditions. The phenotype may vary significantly with variations in environment such as temperature, light intensity and day length.

A Plant Breeder's Right for this cultivar was applied for in the European Union Community Office (CPVO) on Oct. 15, 2013, No. 2013-2676. 'LABZ0006' has not been made publicly available more than one year prior to the filing of this application.

The following traits have been repeatedly observed and are determined to be basic characteristics of the new variety. The combination of these characteristics distinguishes this *Lavandula* as a new and distinct variety.

BRIEF DESCRIPTION OF THE PHOTOGRAPHS

The accompanying photographic drawings show typical flower and foliage characteristics of 'LABZ0006' with colors being as true as possible with an illustration of this type. The photographic drawings show in FIG. 1 a flowering plant of the new variety and in FIG. 2 a flowering plant from an outdoor trial.

DETAILED BOTANICAL DESCRIPTION

The plant descriptions and measurements were taken outdoors in Enkhuizen, Netherlands on Aug. 26, 2014 on about 13 weeks old plants. Rooted cuttings had been planted into 13 cm pots in week 22 (end of May), 2014. The plants were not pinched.

Figure 1:
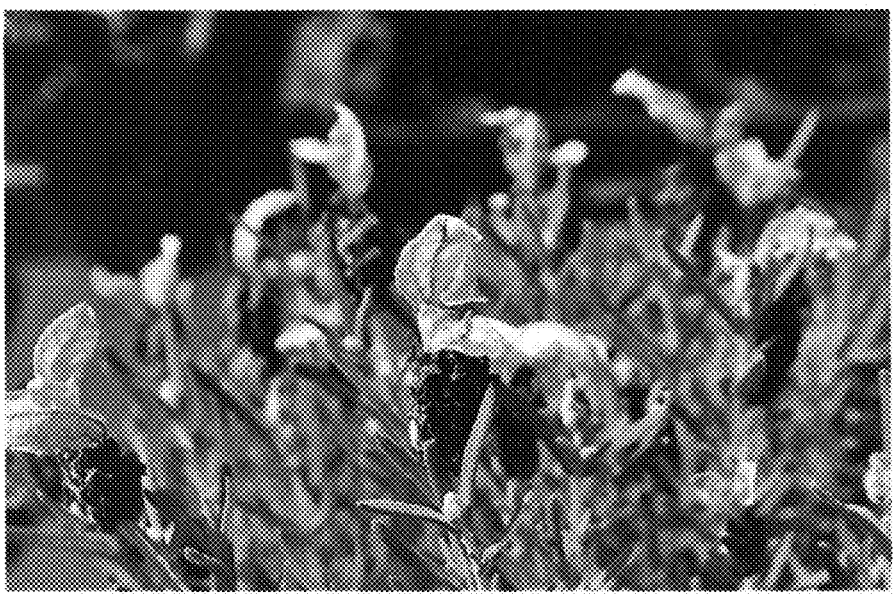
Figure 2:
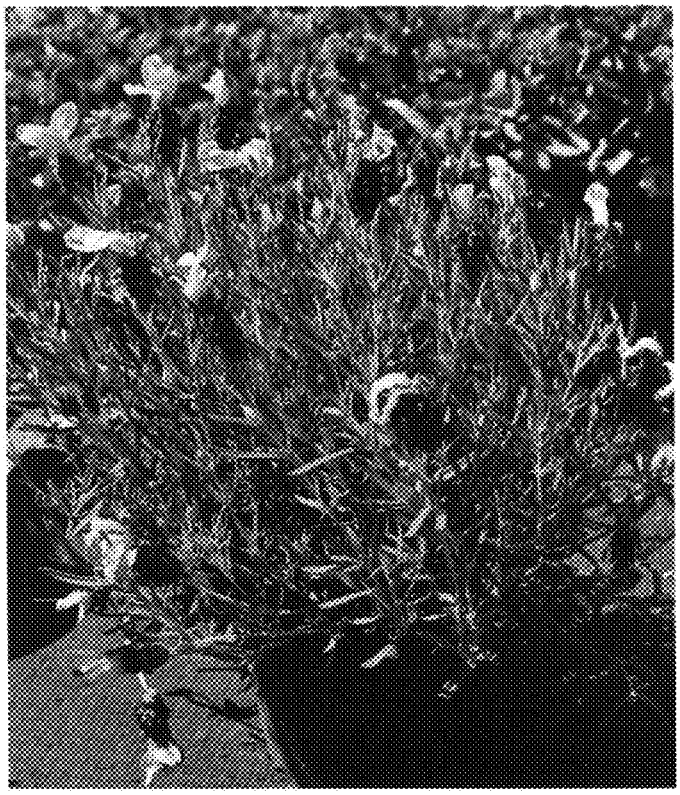

The aforementioned photographs: FIG. 1 was taken in Enkhuizen, Netherlands on Aug. 20, 2013 and showing a closer view of the inflorescences. FIG. 2 was taken in Enkhuizen, Netherlands on Aug. 20, 2013 and showing a plant from an outdoor trial. These plants were about 13 weeks of age. Plants had started flowering naturally by beginning of August.

Color references are made to The Royal Horticultural Society Colour Chart (R.H.S.) 2001.

TABLE 1

DIFFERENCES BETWEEN THE NEW VARIETY 'LABZ0006' AND A MOST SIMILAR VARIETY

| | 'LABZ0006' | 'LABZ0001', commercially Javelin Compact Rose (not patented) |
|---|---|---|
| Plant size: | Taller, more vigorous | Smaller |
| Size of bracts: | 3 cm | 2 cm |
| Number of bracts per inflorescence: | 6-8 | 4-5 |
| Bract color: | RHS 75B, light purple-pink | RHS 76D, distinctly lighter hue |

Plant:

*Plant spread.*—25 cm.

*Plant height.*—30 cm, to top of flowering plane 25 cm to top of foliar plane.

*Growth rate.*—Fast.

*Plant vigor.*—Moderate to robust.

*Length of primary lateral branches.*—16 cm.

*Diameter of lateral branches.*—0.35 cm.

*Quantity of lateral branches.*—About 25.

*Plant habit.*—Dense upright shape.

Stem:

*Juvenile color.*—RHS 137B.

*Mature color.*—RHS 137A.

*Texture/pubescence.*—Densely pubescent.

*Shape.*—Round.

*Strength.*—Very strong and flexible.

*Internode length.*—1.0-1.5 cm.

Propagation and roots:

*Time to initiate roots.*—About 8-12 days at 21 degrees C.

*Time to produce a rooted cutting.*—About 20-25 days at 21 degrees C.

*Root description.*—Fine, fibrous, developing a woody texture with age.

*Color.*—RHS 175A.

Foliage:

*Leaf.*—Arrangement: Opposite. Leaf type: Simple. Quantity: 20 fully expanded per main branch and 25 juvenile leaves. Length: 2.8 cm. Width: 0.3 cm. Shape of blade: Lanceolate. Apex: Acute. Base: Truncate. Attachment: Sessile. Margin: Entire. Texture of all surfaces: Pubescent. Leaf fragrance: Very strong Lavender scent with a hint of clove.

*Color.*—Young foliage upper side: RHS 137B. Young foliage under side: RHS 137C. Mature foliage upper side: RHS 137B. Mature foliage under side: RHS 137A. Venation: Reticulate. Venation color upper side: RHS 144A, only main vein distinguishable from foliage color. Venation color under side: RHS 145B. Petiole: Absent.

Inflorescence:

*Blooming period.*—Late spring to mid-summer.

*Form and shape.*—Small single flower in verticillasters arranged in spikes. Most commonly 7 rows of flowers. Flowers have small bracts, and large showy terminal bracts. One flower spike per lateral stem.

*Number of individual flowers per spike.*—125.

*Fragrance.*—Very strong lavender scent.

*Flower lastingness.*—Individual flowers lasts 1-2 weeks, inflorescence remain ornamental for 4-6 weeks.

*Inflorescence size, excluding terminal bracts.*—Length: 6.0 cm. Width: 2.4 cm. Shape: Cylindrical.

Bud:

*Length.*—0.4 cm.

*Diameter.*—0.2 cm.

*Shape.*—Ovate.

*Color.*—RHS 77D.

*Rate of opening.*—Varies with climactic conditions: 5-10 days from colored bud to open flower.

Corolla:

*Corolla shape.*—Salverform.

*Petal number.*—5.

*Petals fused or unfused.*—Fused at base.

*Petal apex.*—Obtuse.

*Petal base.*—Fused.

*Petal shape.*—Top 2 lobes obovate, lower 3 lobes ovate.

*Petal margin.*—Entire.

*Petal surfaces.*—Glabrous.

*Length.*—0.4 cm (corolla tube).

*Diameter.*—0.2 cm.

*Coloration of individual flowers, excluding terminal bracts.*—Immature: RHS 77D. Mature: RHS 77C, base RHS N155C. Fading: RHS 68D, base RHS N155C.

Bracts:

*Bract shape.*—Elliptic.

*Bract apex.*—Acute with a cusp.

*Bract color.*—RHS 144C, cusp colored RHS 186A.

*Terminal bracts (sterile).*—

*Quantity.*—4 large and 1 or 2 smaller per inflorescence.

Large (terminal) bracts:

*Length.*—3.5-4.5 cm.

*Width.*—1.0 cm.

*Form.*—Petaloid.

*Margin.*—Entire and undulating.

*Surface.*—Smooth.

*Appearance.*—Matte.

*Shape.*—Oblanceolate.

*Apex.*—Acute.

*Base.*—Attenuate.

*Vein pattern.*—Reticulate.

*Color.*—

*Upper side of immature bract.*—RHS 75C, base lighter, RHS 75D. Veins darker, RHS 77A.

*Under side of immature bract.*—RHS 75C Veins darker, RHS 77B.

*Upper side of mature bract.*—RHS 75B.

*Under side of mature bract.*—RHS 75C.

*Bract color fading to.*—RHS 65C.

Small bracts:

*Quantity.*—Typically 2 or 3.

*Length.*—2.0-3.0 cm.

*Width.*—0.7 cm, unfolded.

*Apex.*—Bi-lobe.

*Margin.*—Entire.

*Base.*—Attenuate.

*Aspect.*—Undulating and folded inward at the mid-vein.

*Color.*—

*Upper side of immature bract.*—RHS 75C, base lighter, RHS 75D. Veins darker, RHS 77B.

*Under side of immature bract.*—RHS 75C, base lighter, RHS 75D. Veins darker, RHS 77C.

*Upper side of mature bract.*—RHS 75B.

*Under side of mature bract.*—RHS 75C.

*Bract color fading to.*—RHS 65C.

Calyx:

*Width.*—0.2 cm.

*Length.*—0.85 cm.

*Shape.*—Flattened tube.

*Color.*—RHS 144C.

Peduncle:

*Peduncle length.*—9-11 cm.

*Peduncle diameter.*—0.3 cm.

*Aspect.*—Very straight.

*Color.*—RHS 137C.

*Texture.*—Densely pubescent and ridged.

Reproductive organs:

*Androecium.*—Stamens: 4. Anther length: 0.05 cm. Anther color: RHS N155A. Pollen quantity: Pollen production not observed.

*Pistil.*—Number: 1. Length: 0.4 cm.

*Style.*—Length: 0.3 cm. Color: RHS N155A.

*Stigma.*—Length: 0.05 cm. Color: RHS N77D.

*Ovary.*—Minute and immeasurable.

Other characteristics:

*Seeds and fruits.*—Seed production not observed to date.

*Disease/pest resistance.*—Neither resistance nor susceptibility to the normal diseases and pests of *Lavandula stoechas* has been observed.

*Drought tolerance and cold tolerance.*—Hardy perennial. Tolerates high temperature to at least 36 degrees C. Tolerates low temperatures to degrees 5 C. While specific drought tolerance has not been observed, once plants are established very little water is necessary to maintain plants.

What is claimed is:

1. A new and distinct cultivar of *Lavandula* plant named 'LABZ0006', as substantially illustrated and described herein.

* * * * *